United States Patent [19]

Ring

[11] 3,978,257
[45] Aug. 31, 1976

[54] INTERNALLY ADHESIVELY BONDED FIBROUS WEB

[75] Inventor: David F. Ring, Neenah, Wis.

[73] Assignee: Kimberly-Clark Corporation, Neenah, Wis.

[22] Filed: Aug. 6, 1973

[21] Appl. No.: 385,663

[52] U.S. Cl. ............................... 428/137; 428/198; 428/218; 428/286; 428/288
[51] Int. Cl.² ......................................... B32B 3/00
[58] Field of Search ........... 161/146, 148, 158, 156, 161/157, 170, 151; 156/62.2, 209, 290; 264/119, 128; 429/212, 218, 284, 286, 290, 297, 302, 138, 198, 288

[56] References Cited
UNITED STATES PATENTS

| | | | |
|---|---|---|---|
| 3,660,222 | 5/1972 | Fleming | 161/156 |
| 3,692,622 | 9/1972 | Dunning | 161/148 |
| 3,726,750 | 4/1973 | Stillings | 161/148 |
| 3,733,234 | 5/1973 | Dunning | 161/148 |
| 3,765,997 | 10/1973 | Dunning | 161/148 |
| 3,776,807 | 12/1973 | Dunning | 161/148 |

Primary Examiner—Marion E. McCamish
Attorney, Agent, or Firm—Leydig, Voit, Osann, Mayer & Holt, Ltd.

[57] ABSTRACT

Fibrous material comprised of layers of fibers which are essentially unbonded in their initial formation, bonded by minute, adhesive bonds distributed internally in the material according to predetermined non-uniform Z direction distribution characteristics is produced by sequentially forming fiber layers and applying adhesive between the layers in a manner to introduce adhesive into the layers while leaving the surfaces of the material essentially free of adhesive and solely fibrous. Alternative sequences are disclosed providing different predetermined bond distribution characteristics to obtain different absorbency, tensile and tactile properties. The nonuniformly distributed minute adhesive bonds form an internal three dimensional fiber scrim, and there are disclosed modifications of the material incorporating other two dimensional reinforcements integrated with the three dimensional fiber scrim to enhance tensile strength of the finished material. Also disclosed are composite products incorporating the internally adhesively bonded fibrous material with fluff batts and films. Apertured internally bonded fibrous webs are also disclosed.

10 Claims, 12 Drawing Figures

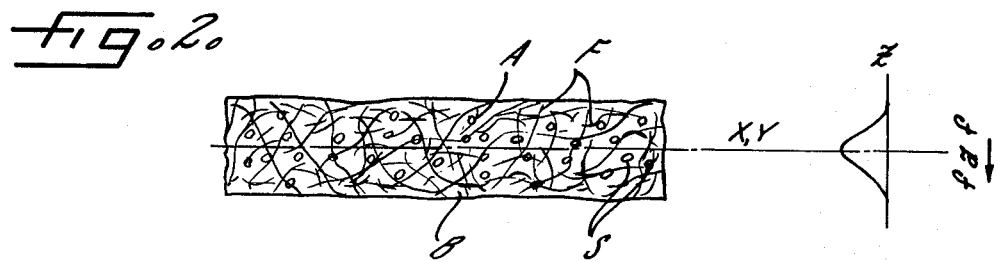
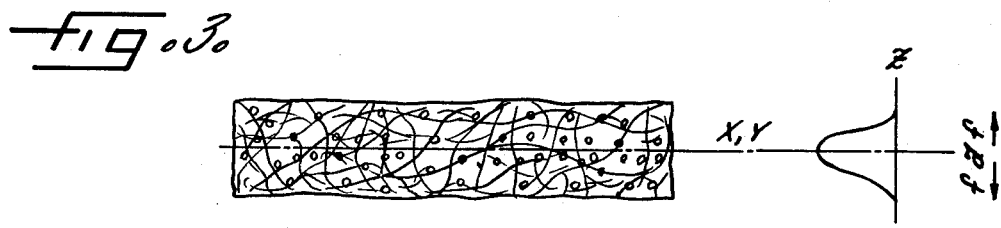
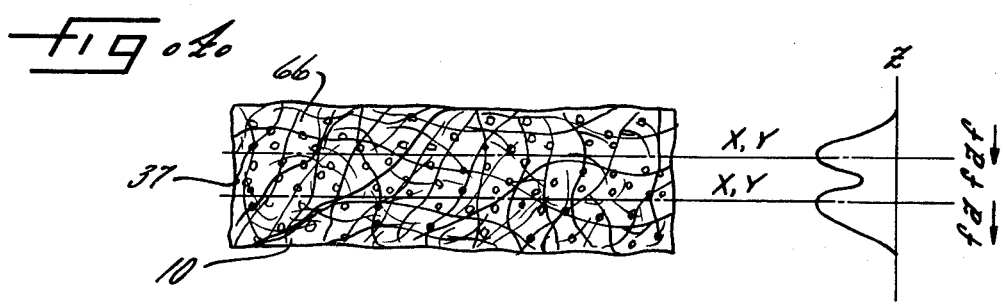
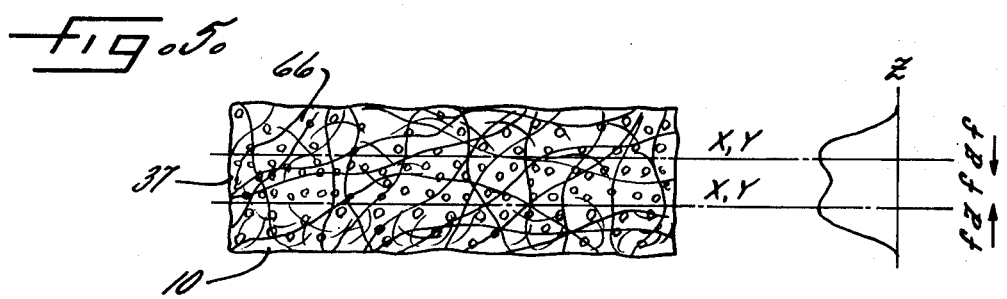
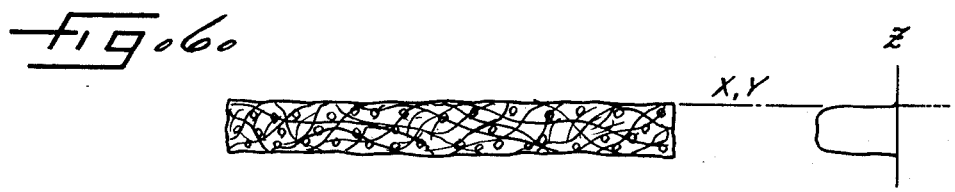
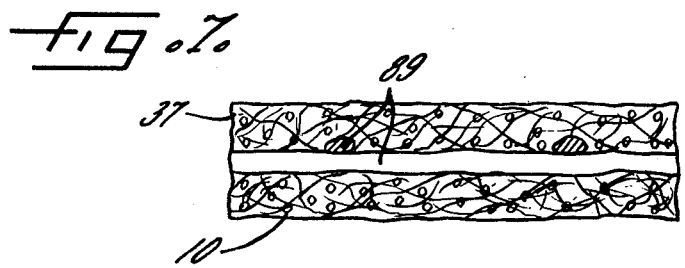

INTERNALLY ADHESIVELY BONDED FIBROUS WEB

This invention relates to the manufacture of flexible internally reinforced fibrous web material having a desirable combination of strength, surface texture and absorbency, and useful for a wide variety of products such as nonwoven fabrics to serve as textile substitutes, sanitary sheet products, wipes and the like.

The principal object of the invention is to provide a fibrous web material which is internally adhesively bonded and a method for manufacturing such material.

More specifically, it is a main object of the invention to provide fibrous web material in which the fibers are bonded by minute, adhesive interfiber bonds concentrated near planes intermediate to the surfaces, and forming an integral three-dimensional internal reinforcement (i.e., a three dimensional fiber scrim) providing superior strength and drapability, open capillary spaces internally for high absorbency and bulk, and soft, adhesive free fibrous surfaces.

A closely related object of the invention is to provide a method for manufacturing such web material on a continuous basis wherein adhesive is introduced into a fiber formation so as to form adhesive bonds at fiber intersections and crossing points, which adhesive bonds are nonuniformly distributed in the Z direction of the formation according to a predetermined bond distribution characteristic, which integrates the fibers into the form of an internal dimensional fiber scrim, while leaving the fibers on the surfaces of the formation essentially free of adhesive to provide web material with soft fibrous surfaces.

Another object is to provide a method which enables the production of such materials having different, specified Z direction bond distribution characteristics to provide web materials having various specified absorbency, strength and tactile properties.

Another object of the invention is to provide a method for manufacturing such web materials which is particularly suitable where short fibers are employed for the initial fiber formation, for example wood pulp fibers, but which is also suitable where longer textile length fibers are employed for the initial fiber formation either exclusively or blended with short fibers. Thus this invention is not limited to the manufacture of web materials from either short or from long fibers but is particularly useful in the manufacture of web materials from short fibers where it has long been a problem to bond the fibers and provide adequate web strength without loss of drapability, softness and absorbency.

Conventional papermaking processes for production of fibrous material from short cellulosic fibers utilize water for laying the fibers and for developing the customary interfiber hydrogen bonds. In the manufacture of cellulose wadding or tissue suitable for sanitary wipes, toweling and nonwoven textile-like materials, the stiffness, harshness and low absorbency of water laid material as produced on the paper machine requires subsequent processing steps such as creping to soften the material and increase its absorbency and bulk by breaking some of the interfiber bonds and opening the surface and internal structure in order to provide material suitable for such applications. It has also been a practice to laminate such water laid material with scrim or webs of textile length fibers to enhance the composite sheet strength, as described for example in Harwood U.S. Pat. No. 3,072,511 and Sokolowski U.S. Pat. No. 3,327,708.

Airlaying processes, or water laying processes wherein the interfiber hydrogen bonds are minimized to produce an essentially unbonded three-dimensional continuum of cellulosic fibers, on the other hand, generally employ adhesive for interfiber bonding. Where adhesive bonding steps are used in such processes, increasing the adhesive content to increase strength, and compressing the material to insure that the short fibers are bonded increases sheet stiffness and reduces the size and frequency of the fluid retaining spaces between fibers and changes their nature because of the introduction into the internal structure of the web of greater amounts of adhesive, resulting in poor absorbency properties. Conversely, decreasing the amount of adhesive to improve drape and absorbency properties decreases strength. In short, there is a drape-strength trade off as adhesive content is increased or decreased and absorbency is also directly affected.

The problem of drape-strength trade off has been long recognized and difficult to solve in the manufacture of web material from short fibers, and it is an important object of this invention to provide a manufacturing method involving forming a web of essentially unbonded short fibers and adhesively bonding the fibers in such a manner as to solve the drape-strength trade off problem and produce material having desirable shape, softness, high absorbency rate and absorbent capacity, and high strength.

A related object is to provide an adhesively bonded short fiber web material having an appearance and hand similar to creped water-laid tissue of facial tissue softness, with substantially higher tensile strength and absorbency rate and absorbent capacity for comparable basis weight.

Another object of the invention is to provide high strength fibrous web material internally reinforced with a combined three-dimensional fiber scrim and two-dimensional scrim.

Another object of the invention is to provide composite products incorporating internally adhesively bonded fibrous web material, such as composites with fluff batts and impervious sheets forming materials suitable for wipes, diapers and like end uses.

Another object of the invention is to provide a method of manufacturing an apertured internally adhesively bonded fiber web.

Other objects will appear from the following description taken in conjunction with the accompanying drawings in which:

FIG. 2 is a cross sectional view which is schematic and highly illustrative of a two layer material constructed in accordance with the invention with a graph and symbols depicting the sequence of fiber formation and adhesive application, and the adhesive bond distribution characteristic for that particular sequence;

FIG. 3 is a cross sectional view which is schematic and highly illustrative of a two layer material constructed in accordance with the invention with a graph and symbols depicting a different sequence than shown in FIG. 2, and the adhesive bond distribution characteristic for that particular sequence;

FIG. 4 is a cross sectional view which is schematic and highly illustrative of a three layer material constructed in accordance with the invention with a graph and symbols depicting the sequence of fiber formation and adhesive application, and the adhesive bond distribution characteristic for that particular sequence;

FIG. 5 is a cross sectional view which is schematic and highly illustrative of a three layer material constructed in accordance with the invention with a graph and symbols depicting a different sequence than shown in FIG. 4, and the adhesive bond distribution characteristic for that particular sequence for a three layer material;

FIG. 6 is a cross sectional view which is schematic and illustrative of a web of fibers which is saturated with adhesive, along with a graph depicting the adhesive bond distribution characteristic for that particular material for comparison with FIGS. 2–5;

FIG. 7 is a cross sectional view which is schematic and highly illustrative of a two layer material with a combined integral fiber scrim and two dimensional scrim;

GENERAL DESCRIPTION OF THE INVENTION

In its broadest aspect, this invention relates to improvements in methods for adhesive bonding of fibrous webs and the resulting improved materials.

Heretofore, adhesive bonding of fibrous webs has been commonly achieved either by applying adhesive in patterns to the surface of a fibrous web with the fibers being embedded in the areas of the pattern, or by saturating the fibrous web with adhesive.

These methods have produced webs characterized by adhesive on at least one of the web surfaces which partially penetrates the web, or fully penetrates through and appears on the other surface of the web, depending on the method of adhesive application, type and amount used.

It is now proposed to adhesively bond fibrous webs internally, such that both surfaces are essentially free of adhesive, and in accordance with a process that introduces adhesive such that it is uniformly distributed in the X and Y directions and nonuniformly distributed in the Z direction of the material, being concentrated near intermediate planes. Superior strength and tactile properties are achieved because the surfaces of the material are essentially free of adhesive and solely fibrous while the adhesive, which is nonuniformly distributed, bonds the fibers at intersections and crossing points and forms an integral reinforcing fiber scrim. Furthermore, by selecting the fiber size and character, adhesive, sequence of fiber formation and adhesive application, controlling the ratio of adhesive/fiber weights, the basis weight of the material and certain other process parameters and precursor material attributes, it is possible with the method of this invention to obtain a range of material characteristics in the areas of strength, absorbency, surface texture, stiffness, bulk and basis weight.

Figure 1:
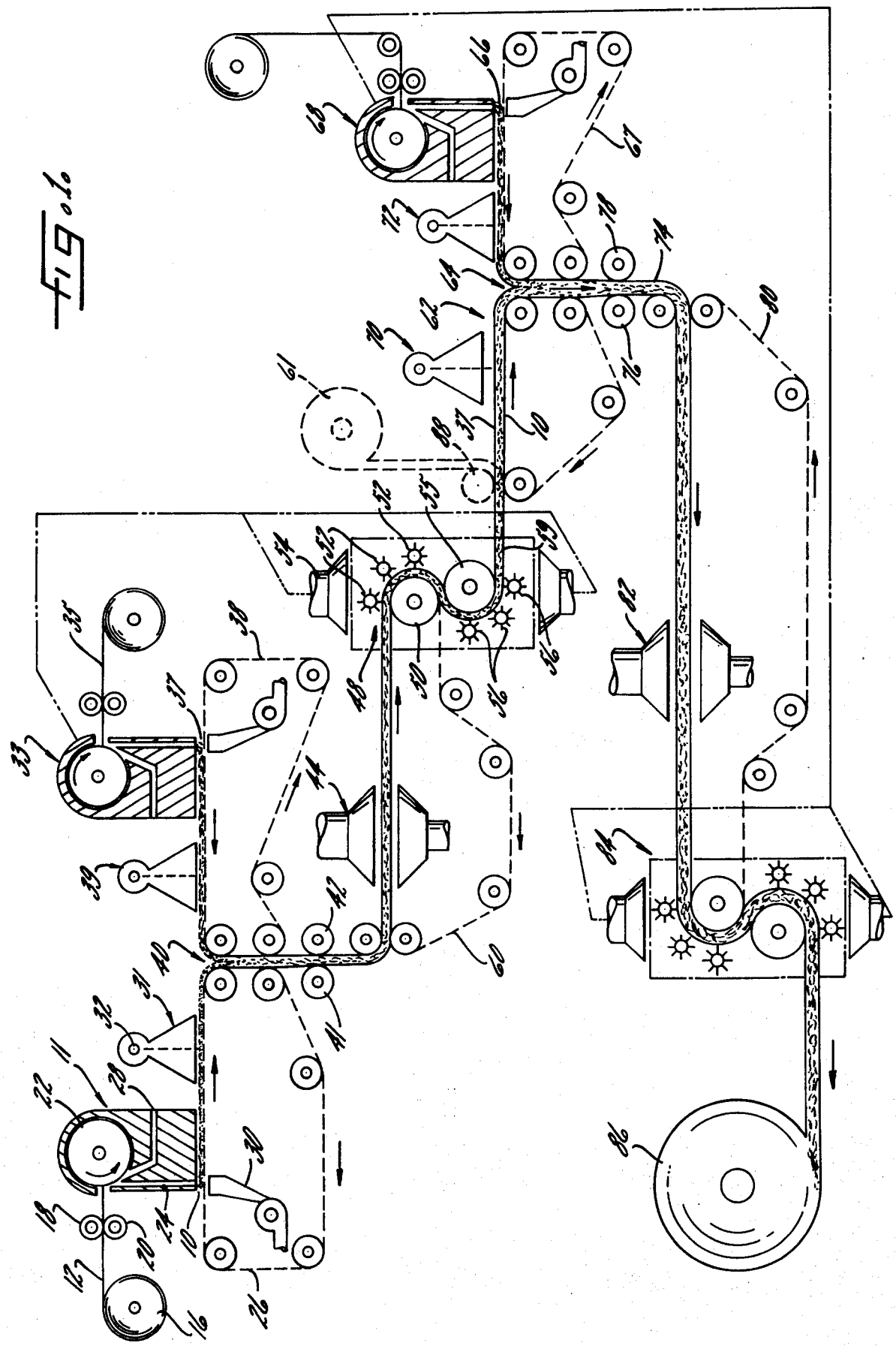
FIG. 1 is a schematic illustration of apparatus to carry out the method of the invention.

As illustrated schematically in FIG. 1, in a preferred form the method of this invention involves; forming a three-dimensional continuum of fibers essentially unbonded in their initial formation; applying adhesive in the form of a fine spray to the surface of the continuum; forming another three-dimensional continuum and applying it to the surface of the adhesively treated first layer; pressing the two layer composite by passing through a light pressure nip; setting the adhesive to fix the interfiber bonds; and removing loose fibers by brushing the surfaces of the material. By carrying out this method, the spaced, fine adhesive drops which are applied to and initially lie on the surface fibers of the first layer, are introduced to interfiber bond sites in both layers by wicking, and are further introduced into both layers to reach additional bond sites by the step of lightly pressing the two layer composite. The adhesive reaches interfiber bond sites at fiber crossings and intersections located internally in both layers with a distribution of adhesive interfiber bond sites which is nonuniform in the Z direction of web thickness, the interfiber bonds being concentrated near the intermediate plane between layers as illustrated by the graph of FIG. 2 which depicts a distribution characteristic in which the concentration of interfiber bonds or bond sites is higher near the intermediate plane and gradual tapers off in successive planes approaching the surfaces of a two layer material. The two layer material A, B, fibers F, and bond sites S are highly schematically also shown in the Figure.

DETAILED DESCRIPTION OF THE INVENTION

A preferred manner of practicing the present invention is shown in FIG. 1. A first layer of fibers 10 is formed in a first forming section 11 by separating a pulp sheet 12 into its individual fibers by unwinding the pulp sheet 12 from a roll 16 and forwarding the sheet by means of the driven rolls 18, 20 to a divellicating means such as a picker roll 22, powered by means not shown. The individual fibers are conveyed through a forming duct 24 and onto a moving foraminous wire 26. Air from a source 28 in combination with a vacuum box 30 creates a downwardly moving stream of air which assists in collecting the air formed fiber layer 10 on the foraminous wire.

While customary air forming techniques can be utilized in forming layers of fibers, the forming duct 24 illustrated in FIG. 1 is efficient in obtaining an especially suitable fiber formation particularly at high speeds. The illustrated duct has a width approximately equal to the height of the picker teeth on the roll 22 and is positioned so as to tangentially receive the fibers as they leave the picker. By using a duct with such a width, fiber velocity can be maintained essentially constant throughout the length of the duct. Fiber layers formed in this manner have exceptionally good uniformity and are substantially free of fiber floccing. Appropriate sizing of the forming duct and the spatial arrangement with respect to the picker and the wire are more completely described in copending Appel application Ser. No. 209,935, filed on Dec. 20, 1971, entitled "Pulp Picking Apparatus with Improved Fiber Forming Duct".

The fiber layer 10 formed in the first forming section 11 on the screen 26 is carried to the right in FIG. 1 through an adhesive applying section 31 herein shown as a spray applicator 32 for adhesive. After the surface of the first fiber layer 10 has been sprayed with adhesive it is carried on the screen 26 and laminated with another fiber layer 37 formed in a second forming section 33 similar to the first forming section 11 in which fibers picked from the pulp sheet 35 are distributed downwardly to form the fiber layer 37 on the screen 38 and carried from right to left in FIG. 1 past a second adhesive applying section 39 which may or may not be activated according to the particular sequence of fiber layer-adhesive applying desired. The two fiber layers 10, 37 are then laminated at 40 with the adhesive between the layers and carried through a nip formed between two rolls 41, 42 and to a through drier 44 to fix the adhesive. The two rolls 41, 42 form a light pressure nip (i.e., 1–100 lb/in.$^2$) which presses the two layers and the fibers therein into more intimate contact with the adhesive droplets on the surfaces between the layers. The two layer material is then carried from the drying section 44 into a brushing section 48. The brushing section includes a first roll 50 around the periphery of which are a series of counter rotating brushes 52 which remove the loose fibers from one surface of the material. The loose fibers are carried into a hood 54 and recycled back to be incorporated into the any one of then acting forming sections 11 or 33. The material passes to the second roll 55 of the brushing section 48 with counter rotating brushes 56 around the surface of the roll working the other surface of the laminate to remove loose fibers, the loose fibers again being recycled back to any air forming section. The material 59 having been removed from the wire 60 may be wound on a roll 61 as finished material; alternatively, the material 59 may be carried to a third section 62 for lamination at 64 to a third layer 66 of fibers formed on the wire 67 by the air laying equipment 68, to produce a three layer material 74 as illustrated in FIGS. 4 and 5. Adhesive may be applied between the central layer 37 of the composite material 59 and the additional layer 66 of fibers, by means of one or both adhesive applying sections 70, 72 which like sections 31, 39 are herein shown as adhesive spray units. After passing the three layer laminate 74 through a light pressure nip between the rolls 76, 78, the material 74 is carried on a screen 80 past a through drier 82 to set the adhesive, into a second section 84 84 similar to the brushing section 48 to remove loose fibers from the surfaces, and the finished three layer material may then be wound on a roll 86.

Figure 8:
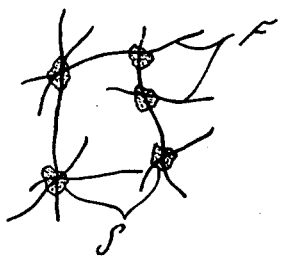
FIG. 8 is a schematic enlarged representation of adhesive interfiber bonds.

In the adhesive applying sections 31, 39, 70, 72, adhesive is introduced in a manner to produce adhesive interfiber bonds internally to develop sheet strength while retaining flexibility, softness, drape and absorbency in the finished product. Discrete, fine adhesive interfiber bonds are produced as distinguished from conventional adhesive bonds developed by print bonding of webs of fibers in which a spot or zone of adhesive is applied in which multiple fibers are embedded. To achieve the desired discrete bonds, the adhesive is preferably applied by a falling spray of microscopic drops. The drops fall on and adhere to the surface fibers with limited penetration into the fiber formation and some degree of adhesive spattering that costs portions of individual fibers, to produce bonds at the crossing points and intersections of fibers as highly schematically illustrated in FIG. 8.

In each adhesive applying section, the spray is preferably applied at low velocity to avoid compacting the fiber formation, and with minimum penetration by force into the formation; the velocity achieved by fine drops of adhesive falling through a distance of between twelve and eighteen inches has been used with good results. If the falling distance is much greater or if velocity is imparted by some means, not only is there undue compaction, but the adhesive drops tend to dry and become more viscous remaining on the surface rather than penetrating by wicking action as desired. A cluster of minute drops may coalesce to form larger drops, but when the adhesive is applied in a very fine spray without sufficient velocity to appreciably compact the continuum, penetration is achieved by lightly pressing the layers in the subsequent pressure nips between rollers 41, 42 or 76, 78 to consolidate the fibers and being them into more intimate contact, such that the adhesive droplets on the surface wick along fibers and through the capillary spaces between fibers into the interior of both adjacent layers of the continuum, and when the adhesive is set the adhesive interfiber bonds are fixed.

This invention is not confined to one method of adhesive application and the best method for a particular employment of the invention will depend on the type of fiber used, the length of fiber, the type of adhesive required, as well as machine speeds and other process parameters, as will be clear to a man skilled in the art. What is regarded to be essential, is the application of adhesive in such a manner as to introduce the adhesive internally within adjacent fiber layers according to a nonuniform distribution characteristic, and this may be achieved in a variety of ways.

It is preferred to apply adhesive in a manner that provides uniform distribution of discrete, minute adhesive bonds per unit area in both the X and Y directions (machine and cross directions) of the material. Thus the tensile strength of any given area of the material will be the same as any other area. It is also preferred to provide substantially the same number of bonds per unit length in both the X and Y directions of the material to produce a material having isotropic tensile strength properties, as by using an overall mist or spray that applies adhesive drops in a random pattern on the surface of the fiber layers. Uniform distribution in the X and Y directions may also be obtained by applying adhesive in an organized pattern as by directing a spray of droplets through a mask or by directing streams of droplets. However, if isotropicity is not a desired or necessary property, the adhesive may be applied so as to achieve uniform distribution per unit area of the material in the X and Y directions, but with a greater number of adhesive bonds per unit length in one direction or the other to achieve a greater tensile strength in the direction of the greater number of adhesive bonds. Furthermore, for interfiber bonding of the nature desired, the spacing of the adhesive droplets should be significantly smalaler than the length of the fibers in the fiber layers, and thus a fine spray or mist of adhesive is used with short cellulose fibers, while with longer natural or synthetic fibers, the adhesive may be applied in a dot pattern with a spacing of between one tenth and one half of the average length of the fibers.

In keeping with the invention, a number of different properties of the finished material can be controlled by adjusting certain variables and process parameters. Thus, finished material suited for a wide variety of end uses can be produced with the method of this invention. The principal physical properties that can be controlled and produced over a range are (a) absorbency (rate and capacity), (b) tensile strength, and (c) flexibility or drape, along with other general properties such as basis weight, bulk and appearance (opaqueness and surface texture).

The main variables and process parameters are (1) type and denier of fibers and structure of the fiber formation (2) adhesive bond distribution characteristic which is a function of adhesive type, method of application and sequence of fiber formation and adhesive application, (3) treatment of fiber layer surfaces by brushing, and (4) incorporation of additional reinforcement.

TYPE AND DENIER OF FIBERS AND STRUCTURE OF FORMATION

When short cellulosic fibers are employed in the process, preferably the layers of fibers are formed by airlaying, but the layers may be formed by water laying techniques. When water laid, however, the fiber formation should have minimum interfiber hydrogen bonds of the type customarily present in self bonded paper products. This may be achieved either by disrupting such bonds if present in the initial formation, or by chemical treatment or process steps to preclude the formation of such bonds. The initially unbonded fiber formation, therefore, will ordinarily be extremely weak, flimsy and not sustaining, but heavier and stronger webs with sufficient strength to be self-sustaining for handling in their initial formation may be used in the process provided that the internal arrangement of fibers is sufficiently open to permit the introduction of adhesive internally to achieve the requisite internal bonds. The process of this invention is particularly suited to the manufacture of light weight webs (10–100 gr./m$^2$) from short cellulosic fibers, such webs being suited for uses ranging from facial tissue through textile substitutes.

Where longer natural or synthetic fibers are employed in the process, the layers of fibers may be formed with conventional web forming equipment such as carding, garnetting, airlaying or other mechanisms. The fibers in the layers as formed are preferably disposed in haphazard arrangement although they may tend to be disposed with a predominant orientation in the machine direction of the web. It is important to operate the forming equipment so that the fibers of each layer have a Z direction component and the fibers which lie on the surfaces of the layers extend at least partially into the interior of the layers, such that the internal adhesive bonds are effective to bond the surface fibers. Webs of longer fibers may be relatively heavy weight as well as light-weight, upwards of 200 gr./m$^2$.

To achieve higher rates of absorbency, natural or synthetic fibers which are of a type wettable by the particular liquid to the absorbed (water, oil, organic solvents) are chosen rather than fibers of a type non-wettable by the particular liquid. An open fiber surface with an internal pore structure providing capillary passages to the interior of the layers is preferable over a surface with the fibers tightly packed and with plugged pores internally. One of the steps of the method of this invention involves brushing the surfaces of the material in the brushing sections 48 or 84 to remove loose unbonded fibers. These brushing steps also serve to open the surface to facilitate achieving high rates of absorbency. Furthermore, a formation of fibers with a significant Z direction component and with the fibers held in their open structure against collapse by minute adhesive bonds, which is a further feature of the invention, will provide for higher rates of absorbency.

Conversely, absorbency rate will drop with fibers which are non-wettable and laid in more tightly packed formation on the surface. Thus even when brushed to remove loose fibers, the remaining fibers on the surface tend to block liquid inflow.

To achieve material with high wet bulk, it has been found important to select fibers which when wetted by the liquid being absorbed do not collapse and decrease the pore and capillary size. For example, fibers of cellulose cross linked by urea and formaldehyde tend to retain their structural integrity and do not collapse when wetted with water in the manner of ordinary cellulose fibers. When such cross linked cellulose fibers are utilized to form the layers of material, and bonded in accordance with the method of this invention, a material will be produced having higher wet bulk than the same material with ordinary cellulose fibers. For higher wet bulk with liquids other than water, best results will be obtained with fibers which maintain structural integrity and do not collapse when wetted by the liquid being absorbed.

The ability of a material to absorb and retain liquid is determined not solely by the volume of the internal pores and capillary passages initially present in the material but also what occurs to the structure of the fibers as the liquid is absorbed. With this method of introducing an internal three dimensional adhesive scrim, fibers are held by the internal adhesive bonds in their initial formation; if the initial formation has a high volume of voids and passages, and the fibers are held in their formation by the fiber scrim, and the fibers themselves are constituted so as not to collapse when wetted by the liquid, a material of high absorbent capacity will be the result.

Another way of utilizing the invention to produce a product with higher absorbent capacity is to produce a material as illustrated in FIG. 2 that will pass liquid readily and use that material as a cover for an absorbent pad of fluff or the like. The material may be either physically held in intimate contact with the surface of the pad or integrated with the pad as desired. In this case, the ability of the material to pass liquid is utilized and the retention of the liquid is a function served by the pad. In the case of an integrated material, adhesive may be applied to one surface of the finished material illustrated in FIG. 2 and a preformed pad of cellulose wadding or the like adhesively attached to the material. Alternatively, the adhesive may be applied to one surface of the finished material shown in FIG. 2, and a layer of fluff deposited on the adhesive bearing surface for attachment of the fluff to the surface of the material. The fluff layer becomes the absorbent layer and when internally disposed with the finished material of FIG. 2 on one side and an impervious plastic sheet on the other will provide, for example, an integrated diaper material, as described more fully hereinafter in the section "Further Embodiments".

Adhesive Bond Distribution Characteristic

Figure 11:
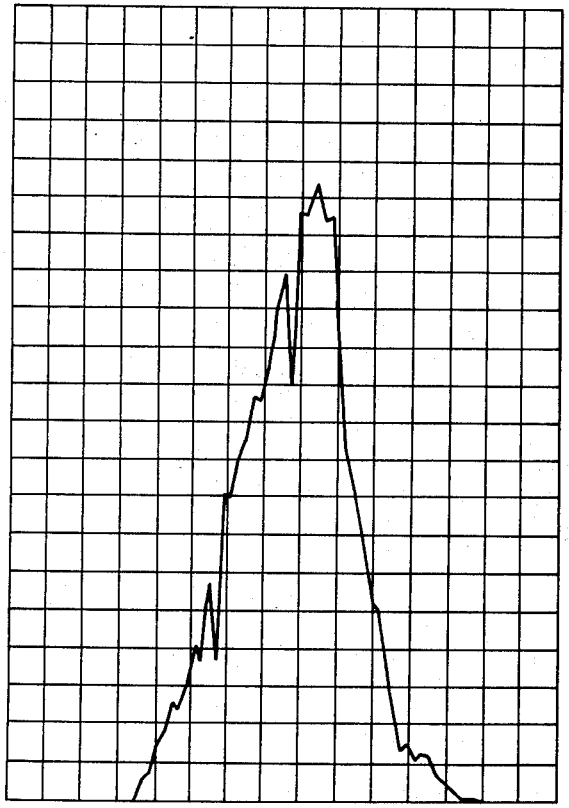
FIG. 11 is an illustrative graph of measurements of adhesive bond area as a percent of total area taken in closely spaced planes parallel to the surfaces of an f a f material.

An important factor that affects absorbency, tensile strength and drape is the adhesive bond distribution characteristic. By following the method of this invention, adhesive is introduced into the fiber formation by wicking along fibers and through capillary spaces such that the adhesive is concentrated near the planes intermediate the layers of fibers, and is present at a progressively decreasing number of fiber intersections and crossing points in planes incrementally spaced away from the intermediate planes. The graph of FIG. 2 shows a characteristic curve of bond distribution for a two layer material made with the method of this invention. The curve shows nonuniform distribution with a concentration of bonds near the midplane of a two layer material and the number of bonds gradually tapering off towards the surfaces of the material. The characteristic curve of bond distribution for a sample of material may be verified by conventional microtoming techniques, involving embedding the finished material in resin, microtoming the sample along closely spaced planes parallel to the surfaces and measuring the area occupied by the adhesive bonds over a given unit area in each plane. FIG. 11 is a plot of actual data points taken in that manner with the adhesive bond area as a per cent of total area being plotted on the vertical axis and the spacing of the planes being plotted on the horizontal axis of the graph. The graphs of FIGS. 2-6 are idealized representations of various adhesive bond distribution characteristics, while graphs of raw data will have the variations from the ideal typified by FIG. 11.

The form of the characteristic curve is affected by the type of adhesive utilized and its method of application. It is preferred to apply the adhesive by spraying and adhesives in aqueous dispersions or solutions or solvent systems which can be sprayed and which are effective to bond the types of fibers used, are generally suitable.

Examples of adhesives for application to cellulose fiber webs include acrylic latexes, various starches, water soluble polymeric materials, and water dispersible resins such as various vinyl resins (e.g. polyvinyl acetate and vinyl acetate/ethylene copolymers). Adhesives such as vinyl resins and polyurethane in suitable organic solvent carriers can also be employed. In addition, plastisols, i.e., polymeric materials such as vinyl polymers (e.g. vinyl chloride) and copolymers dispersed in fluid plasticizers such as dioctyl phthalate and the like can also be used at suitable viscosities. Moreover, the process is not limited to spray application of adhesive, for adhesives such as polyurethane which are available in powdered form can be applied by sprinkling or blowing on the fiber layers. Since the introduction of the adhesive into the layers when the adhesive is applied in liquid form is primarily by wicking, it is recognized that the penetration may not be as extensive when the adhesive is applied in powdered form although when applied in very fine particulate form the general bond distribution characteristic illustrated in the graph of FIG. 2 may be obtained with a two layer material. To achieve this result where the adhesive particles are in solid form, flowing air or other gas in the Z direction through the formation or other externally applied means may be utilized in place of or in addition to the step of external pressure applied by pressing rolls for introducing the particles to the bond sites within the formation according to the required nonuniform distribution characteristic in the Z direction. Adhesive may also be applied in the form of liquid emulsion or foam to the fiber layer, and in this case wicking is utilized to introduce the adhesive into the fiber layer to achieve the desired nonuniform distribution of bonds in the Z direction. In this manner the general bond distribution characteristic shown in the graph of FIG. 2 for a two layer material may be obtained. Powdered adhesives such as polyurethane and foams or liquid emulsions of the resins mentioned above and other adhesives may be used, depending on the type of fiber and the bond distribution characteristic desired.

The form of the adhesive bond distribution characteristic curve is a function of the sequence of fiber formation and adhesive application as well as a function of the adhesive type and method of application. Thus, referring again to FIG. 2, the sequence of fiber formation and adhesive application is f $\bar{a}$ f which symbolically represents that a first fiber layer is formed and adhesive is sprayed on that fiber layer followed by the association of a second fiber layer on the sprayed surface of the first as illustrated in the first two sections 11 and 33 of FIG. 1, with one of the adhesive applying sections 31 or 39 being inactive.

Now referring to the graph of FIG. 3, a bond distribution characteristic having a higher peak than that shown in FIG. 2 indicating a greater concentration of adhesive bonds near the midplane between the two layers of fibers is graphically illustrated in that Figure. This is achieved by a different sequence of fiber formation and adhesive application than symbolically represented in FIG. 2. As symbolically described in FIG. 3, the sequence is f $\bar{a}$ f. This represents that with the apparatus of FIG. 1, a fiber layer 10 formed on the screen 26 by means of the forming section 11 is carried from the left in FIG. 1 through the adhesive applying section 31, while a similar fiber layer 37 formed on the right in FIG. 1 by means of the forming section 33 is carried past a second adhesive applying spray apparatus 39. In this case both adhesive applying sections 31 and 39 are activated. The two fiber layers 10, 37 are then laminated at 40 with the adhesive bearing surfaces face to face and carried through the nip formed between the two rolls 41, 42 and to a through drier 44 to set the adhesive. The two layer material then passes through the brushing section 48 to brush both surfaces of the material, with recycling of the removed fibers. The finished two layer material is then removed by carrying it around the guide roll 88 to the finished material roll 61. With a process like that illustrated in FIG. 1 to produce a material diagrammatically illustrated in FIG. 3, a greater concentration of adhesive bonds is achieved near the mid plane of the finished sheet because of the increased adhesive applied to the fiber layers through the two spray applications. In general, however, the bond distribution characteristic curve is the same as in FIG. 2 with the peak near the mid plane of the sheet and a tapering off toward both surfaces. Both surfaces are soft and essentially free of adhesive being solely fibrous. FIG. 11 is a plot of raw data showing bond distribution in an f $\bar{a}$ f sample.

Now referring to FIG. 4, this illustrates a three layer material and its adhesive bond distribution characteristic, produced with all three forming sections 11, 33 and 68 and two adhesive applying sections 31, 70 of FIG. 1 (adhesive applying sections 39 and 72 in this case are not active). As represented symbolically in FIG. 4, the adhesive fiber formation sequence is f $\bar{a}$ f $\bar{a}$ f. This symbolically represents that the fiber layer 10 on the bottom in FIG. 4 is first formed in the fiber forming section 11 schematically shown in FIG. 1 and adhesive is applied by the spray apparatus 32 on the surface of the first layer. A second layer of fibers 37 is laminated to the first using the second forming section 33 and the laminate is pressed between the rolls 41, 42, dried in the drier 44 and brushed in the brushing section 48. The material 59 is carried to the adhesive applying section 70 and the material is laminated at 64 to the third layer 66 of fibers. The three layer material is then passed through a light nip formed by the rollers 76, 78 and dried in the drier 82 to set the adhesive; the three layer material is then passed through a brushing section 84 to remove loose fibers from the surfaces of the material. The bond distribution characteristic illustrated in the graph of FIG. 4 shows a two peaked curve, the peaks occurring at the planes intermediate the layers. The concentration of bonds drops off in the central layer 37 but because of the sequence of adhesive application, the adhesive from the first application is introduced into the central layer 37 through wicking action, and the adhesive from the second adhesive application is applied directly to the central layer, penetrates the layer and is introduced through wicking action into that layer. Thus, adhesive bonds will be distributed completely through the central layer but the bonds will be more highly concentrated near the intermediate planes between layers.

As shown in the graph of FIG. 5, another form of adhesive bond distribution characteristic somewhat different from that shown in FIG. 4 may be produced in a three layer material by following the sequence of fiber formation and adhesive application represented symbolically in FIG. 5 as f a f a f. This symbolically represents that with the apparatus of FIG. 1 the central fiber layer 37 is sprayed on one surface in the adhesive applying section 39 and a layer of fibers 10 which has not been sprayed (the adhesive applying section 31 being inactive) is applied, the central layer 37 (after pressing, drying and brushing) is sprayed on the opposite surface in the adhesive applying section 70 and a third layer of fibers 66 is then laminated thereto, and the three layer composite is then lightly pressed, the adhesive cured and the surfaces of the material brushed to provide two finished surfaces by removing all loose fibers and leaving essentially adhesive free solely fibrous surfaces. As thus described, the FIG. 5 material is made utilizing the adhesive applying sections 39 and 70 and by leaving inactive the adhesive applying sections 31 and 72. In this case, because the adhesive is applied directly to the central layer 37 from both sides, the adhesive bond distribution characteristic shows a more or less uniform concentration of bonds through the central layer as contrasted with the characteristic distribution curve shown in FIG. 4 where the concentration of bonds in the central layer dropped off significantly toward the middle of that layer.

FIG. 6 is included to demonstrate a bond distribution characteristic typical of a fully saturated fibrous formation. Saturation may be obtained by dipping a fiber web in a bath of adhesive or by spraying so heavily as to fully saturate the material throughout. The characteristic bond distribution curve shown in that Figure may be contrasted with the characteristic bond distribution curves of FIGS. 2–5. In the case of FIG. 6, the bond distribution curve shows bonds on the surfaces, substantially uniform bond distribution in the Z direction of the sheet, and does not show the gradual tapering off from a greater concentration of bonds near one or more intermediate planes as illustrated graphically for the examples of FIGS. 2–5. When a fibrous sheet is saturated with adhesive, some wicking of the adhesive at the surface into the interior may be expected, but not to the extent that the surface becomes adhesive free.

Absorbency of the material is influenced by the sequence of fiber formation and adhesive application, and also by the ratio of adhesive/fiber content of the sheet. Thus comparing FIGS. 2 and 3, for example, with less adhesive in the composite two layer material (FIG. 2) due to the single spray application, and a lower ratio of adhesive/fiber content of the sheet, the sheet of FIG. 2 will tend to have a higher absorbent capacity. Applying additional adhesive (FIG. 3) does tend to plug the capillary passage in the material. However, the physical properties of flexibility and tensile strength are also highly influenced by the sequence of fiber formation and adhesive application. Thus the sheet of FIG. 3 will tend to have a higher tensile strength and be stiffer than the sheet of FIG. 2. Comparing the sheets of FIGS. 4 and 5, while absorbent capacity may be similar for these two sheets since the ratio of adhesive/fiber content will be essentially the same with two spray applications having been utilized in the formation of both sheets, the tensile strength characteristics of the two materials will be different. FIG. 5 with the more uniform distribution of bonds through the central layer will tend to have a greater tensile strength than the material of FIG. 4 in which the distribution characteristic is clearly nonuniform through the central layer. The amount of adhesive added to achieve internal bonding will vary with the type of adhesive used, the type of fiber, and the tensile strength - drapability desired. It has been found that the ratio of adhesive/fiber will vary from about 1/10 to about 1/1 depending on these and other factors.

BRUSHING TREATMENT

Another factor which when varied affects absorbent rate and absorbency is the step of brushing the surfaces of the material. While in the foregoing description there was intermediate brushing in the section 48 in the formation of the three layer material, this invention contemplates that this intermediate brushing step is preferred, but not mandatory. The purpose of brushing before application of the third layer is to remove loose fibers and thus open up the internal pore structure when a subsequent layer is applied and to insure that the fibers on the surface that will receive the third layer of fiber are adhesively bonded to strengthen the sheet against subsequent delamination.

Brushing is also carried out as a step to remove unbonded fibers from the outer surfaces of the finished material. While mechanical brushing is illustrated, air streams or the like may be used to brush the loose fibers from the surface of the material. In the case where material is manufactured for an end use in which only one surface is to be exposed, the other surface may be left unbrushed. This will mean that unbonded fibers on one surface remain in the material, increasing the fiber content of the sheet. Where the fiber formation is not intense and packed, this provides additional small voids and capillary passages and increases the absorbent capacity of the sheet.

FURTHER EMBODIMENTS a. Incorporating Additional Reinforcement

The introduction of adhesive into the fiber formation in accordance with the various sequences of fiber formation and adhesive application illustrated in FIGS. 2–5 results in the production in each of those materials of an internal three-dimensional fiber scrim extending into adjacent layers. In carrying out a further aspect of the invention, an independent reinforcement 89 such as a very light denier two dimensional scrim, light continuous filament or carded web, or apertured film may be incorporated between the fiber layers of the material and integrated with the three dimensional fiber scrim. Such a material is illustrated in FIG. 7. In the manufacture of material incorporating an independent reinforcement, the adhesive is not only introduced into the two layers to develop the three dimensional scrim but also serves to attach and bond the fibers at the planes between the layers to the two dimensional reinforcement. This will enhance the tensile strength of the material although it will tend to stiffen the material, providing a very strong textile like material. Such reinforcing webs may be introduced at the juncture 40 in the apparatus of FIG. 1 between the adhesive sprayed surfaces of fiber layers 10, 37 to modify the sequence represented as f'a'f in FIG. 3.

b. Combined with Pad

Figure 9:
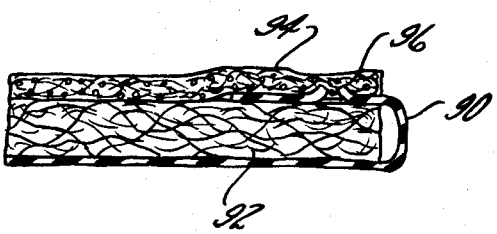
FIG. 9 illustrates an edge sealed composite product.

Another way of utilizing the invention in absorbent products is to take an internally bonded material as illustrated in any one of FIGS. 2–5 or 7 that will pass liquid readily and use that material as one element of a composite product also including an absorbent cellulosic fiber pad. The internally bonded material may be either held in intimate contact with the surface of the pad or attached to the pad. In either case, the ability of the internally bonded material to pass liquid is utilized and the retention of the liquid is a function served by the pad. In the manufacture of such a composite product, an open pattern of adhesive may be applied to a surface of one of the finished materials illustrated in FIGS. 2–5 or 7, and a preformed pad of cellulose fibers, wadding or the like adhesively attached to the material. Alternatively, the pad and internally bonded material may be left unattached to each other. The composite so formed may be used as such in absorbent products, or with a sheet of fluid impervious film or cellulosic wadding on the opposite surface of the pad, the composite product is suitable for mats, wipes, diapers and like products. As shown in FIG. 9, a sheet 90 such as impervious film may be folded over the edge of the pad 92 and introduced between the pad and the internally bonded material 94 and attached to the latter as by a heat sealed seam 96. An integrated diaper may be made by constructing the four edges of a rectangular piece of such composite product in the manner shown in FIG. 9.

c. Combined with Fluff

As a still further embodiment, adhesive may be applied to one surface of internally bonded material as shown in FIGS. 2–5 or 7, and a fluff batt laid directly on the adhesive bearing surface. The fluff layer or fluff batt may have a thickness of between 0.10 and 1.5 inches and be an unbonded, fluffy low density material which becomes the absorbent layer. On the opposite surface of the fluff layer a further layer of internally bonded material of the type shown in FIGS. 2–5 or 7 may be applied to produce a mat or wipe, or a sheet of impervious film or wadding may be applied on the opposite side and inserted and attached at the edge as illustrated in FIG. 9 to provide, for example, a wipe or an integrated diaper.

d. Apertured Material

Figure 10:
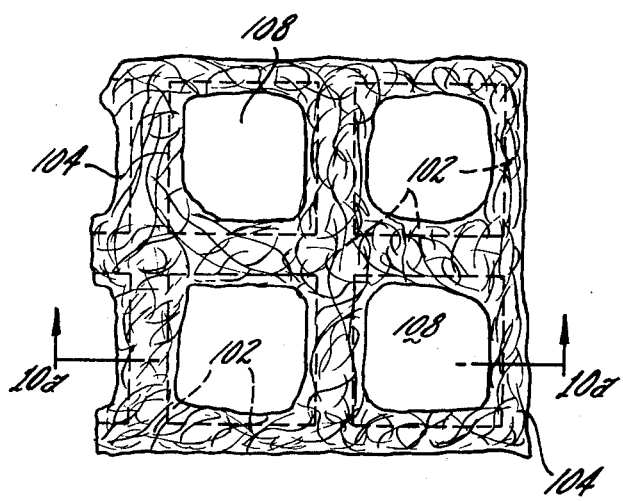
FIG. 10 is an illustration in plan view of an example of apertured material made in accordance with the invention.
Figure 10A:
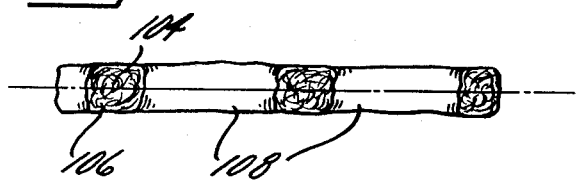
FIG. 10a is an enlarged cross-sectional view of the material of FIG. 10 taken in the plane of lines 10A—10A.

This invention provides a method for manufacturing apertured fibrous materials, as a further embodiment thereof. This may be achieved by applying adhesive by spraying through a mask, by directing streams of adhesive droplets, or by applying adhesive by means of a screen coated with a release material such as Teflon, onto the surface of a fiber layer 100 to achieve a reticulated pattern (see shaded area in FIG. 10) having continuous bands 102 of adhesive extending both longitudinally and transversely of the initial fiber layer, and defining adhesive free areas enclosed within the adhesive bands. The bands or lines have finite width illustratively ⅛ inch and the spacing across the adhesive free areas between adhesive bands or lines is illustratively ¼ inch. As in the previous forms of the invention, after a second fiber layer 104 (FIG. 10A) is applied to the adhesive bearing surface of the first layer 106, the two layer formation is removed from the forming wire, pressed, the adhesive dried, and then brushed. In the brushing section, brushing to remove unbonded surface fibers is also effective to remove unbonded fibers within the adhesive free areas of the reticulated adhesive pattern to form the apertures 108, and the fibrous structure has the essentially adhesive free surfaces and internal bonds that characterize products constructed in accordance with the invention. Such an apertured two layer material may be subsequently carried through successive adhesive applying, fiber forming, pressing, adhesive setting and brushing steps to produce a three or more layer apertured material having bonds distributed internally according to a bond distribution characteristic as shown in FIGS. 4 or 5, the bond distribution being measured in a section through the bonded fiber areas.

Such an apertured material is useful as a high bulk wipe, or as a diaper liner or feminine hygiene pad cover where the material serves to allow liquid flow through the material while stopping liquid flow across the material.

The following table compares various conventional materials with specific examples I–VI of internally bonded material constructed in accordance with the invention; examples I–III have the structure of FIG. 3, and example IV has the structure of FIG. 4.

|  | Tensile gr/cm Dry MD | Dry CD | Basis Weight gr/m² | % Stretch % stretch | Absorbency gr/gr | Thickness | lint[3] count | stiffness Mg. MD (CD) |
|---|---|---|---|---|---|---|---|---|
| Conventional nylon scrim reinforced tissue towel | 602 | 212 | 80 | 19% | 6.05 | .043 | 144 | 59.9 (39.9) |
| Conventional kitchen tissue towel 2 ply | 376 | 184 | 44 | 17% | 5.56 |  | 196 | 28.9 (22.2) |
| Conventional facial tissue 2 ply | 184 | 55 | 16 |  | 5.86 | .0052 |  | 1.1 (.8) |

-continued

|  | Tensile gr/cm Dry MD | Tensile gr/cm Dry CD | Basis Weight gr/m² | % Stretch % stretch | Absorbency gr/gr | Thickness | lint[3] count | stiffness Mg. MD (CD) |
|---|---|---|---|---|---|---|---|---|
| Conventional heavy duty tissue towel | 538 | 302 | 57 | 22.9% | 6.28 | .038 | 152 | 71.0 (57.7) |
| Example I | 1080 | 1080 | 80 | ↑ | 5.4 |  | ↑ | 19.8 |
| Example II[1] | 450 | 450 | 45 | ~16% | 7.5 |  | ~62 | 4.8 |
| Example III[2] | 820 | 820 | 80 | ↓ | 5.0 |  | ↓ | 10.6 |
| Example IV[1] | 920 | 920 | 80 |  | 6.2 |  |  | 26.0 |
| Example V[1] | 160 | 160 | 16 | 16% | 9.0 |  | ~60 | .5 |
| Example VI[2] | 40 | 40 | 16 | ↑ |  |  |  |  |

[1]Higher pressing nip pressure, about 3 lb/inch²
[2]Lower pressing nip pressure, about 1 lb/inch²
[3]Particles larger than 10 microns

I claim:

1. An internally adhesively bonded fibrous material having a basis weight of between about 10 to about 100 grams per meter² comprising layers of substantially non self bonded fibres, and minute, adhesive interfiber bonds distributed nonuniformly in the Z direction of the material and forming an integral, three dimensional internal fiber scrim, said interfiber bonds being distributed according to a distribution characteristic curve with peaks and a gradual tapering off away from the peaks representing high bond concentration near the planes intermediate the fiber layers and progressively lower bond concentration approaching both surfaces of the material, the surfaces of the material being essentially adhesive free and solely fibrous.

2. An internally bonded fibrous material according to claim 1 comprising three layers of fibers with adhesive interfiber bonds distributed according to a distribution characteristic curve with two spaced peaks and a depression between the peaks representing a high concentration of bonds near the two planes intermediate the three layers, and a lower concentration of bonds near the mid plane of the central layer of fibers.

3. An internally adhesively bonded fibrous material having a basis weight of between about 10 to about 100 grams per meter² comprising layers of substantially non self-bonded fibers, the fibers immediately adjacent and on both sides of planes intermediate said layers having adhesive thereon providing discrete, adhesive internal interfiber bonds uniformly distributed per unit area in the X and Y direction of the material, and nonuniformly distributed in the Z direction of the material according to a characteristic curve with peaks and a gradual tapering off in both directions away from each of the peaks representing a high concentration of interfiber bonds near and on both sides of the planes intermediate the fiber layers and a progressively lower concentration of interfiber bonds approaching the surfaces of the material, said bonded fibers forming an integral, three dimensional internal fiber scrim extending into both layers from an intermediate plane and said internal interfiber bonds bonding the surface fibers, the outer surfaces of the material being essentially adhesive free and solely fibrous.

4. A fibrous material according to claim 3 wherein said adhesive interfiber bonds are distributed substantially equally in the X and Y directions to provide a material having substantially isotropic tensile strength properties.

5. An internally adhesively bonded fibrous material having a basis weight of between about 10 to 100 grams per meter² comprising layers of substantially non self bonded fibers, and minute, adhesive interfiber bonds distributed nonuniformly in the Z direction of the material and forming an integral, three dimensional internal fiber scrim, said bonds being distributed according to a distribution characteristic curve with peaks representing high bond concentration near and on both sides of the planes intermediate the fiber layers and a gradual tapering off in both directions away from each of the peaks representing progressively lower bond concentration approaching the surfaces of the material, the outer surfaces of the material having been brushed to remove loose fibers and comprising internally bonded fibers and being essentially adhesive free.

6. An internally adhesively bonded fibrous material having a basis weight of between about 10 to about 100 grams per meter² comprising layers of substantially non self bonded fibers with the fibers bonded by minute, discrete, adhesive interfiber bonds uniformly distributed in the X and Y directions of the material, and nonuniformly distributed in the Z direction of the material, the adhesive bonds being concentrated near the planes intermediate the fiber layers and there being a progressively lower concentration of bonds approaching the surfaces of the material, said minute, discrete, adhesive interfiber bonds forming an integral, three dimensional internal fiber scrim extending into both adjacent layers from an intermediate plane while at least one of the surfaces of the material has been brushed to remove loose fibers and comprises internally bonded fibers, the outer surfaces being essentially adhesive free.

7. An internally adhesively bonded fibrous material having a basis weight of between about 10 to about 200 grams per meter² comprising layers of substantially non self bonded fibers, and minute, adhesive interfiber bonds distributed nonuniformly in the Z direction of the material and forming an integral, three dimensional internal fiber scrim, said bonds being distributed in the Z direction according to a distribution characteristic curve with peaks and a gradual tapering off in both directions away from each of the peaks representing high bond concentration near and on both sides of the planes intermediate the fiber layers and progressively lower bond concentration approaching the surfaces of the material, and the outer surfaces of the material having been brushed to remove unbonded fibers providing material with surfaces essentially adhesive free and solely fibrous.

8. An internally bonded fibrous material according to claim 7 in which said fibers are cellulose fibers of papermaking length, and said material has a basis weight of between about 10 to about 100 grams per meter².

9. An apertured internally adhesively bonded fibrous material having a basis weight of between about 10 to about 100 grams per meter² comprising layers of substantially non self bonded fibers, and minute, adhesive interfiber bonds distributed in a reticulated pattern in the X and Y directions and nonuniformly in the Z direction of the material and forming an integral, three dimensional internal fiber scrim, said bonds being distributed in the Z direction according to a distribution characteristic curve with peaks and a gradual tapering off in both directions away from each of the peaks representing high bond concentration near and on both sides of the planes intermediate the fiber layers and progressively lower bond concentration approaching the surfaces of the material, the reticulated bond pattern defining uniformly spaced adhesive free areas in the X and Y directions, and the surfaces of the material having been brushed to remove unbonded fibers from the adhesive free areas and the surfaces, providing an apertured material with surfaces essentially adhesive free and solely fibrous.

10. A composite pad comprising:
a. an internally bonded fibrous material having a basis weight of between about 10 to about 100 gr./meter² comprising layers of substantially non self bonded fibers, and minute, adhesive interfiber bonds distributed nonuniformly in the Z direction of the material and forming an integral, three dimensional internal fiber scrim, said bonds being distributed according to a distribution characteristic curve with peaks and a gradual tapering off away from the peaks representing high bond concentration near the planes intermediate the fiber layers and progressively lower bond concentration approaching the surfaces of the material; and
b. a fluff batt substantially coextensive with and disposed adjacent one surface of said fibrous material.

* * * * *